United States Patent [19]

Bryant et al.

[11] Patent Number: 5,741,945
[45] Date of Patent: Apr. 21, 1998

US005741945A

[54] PROCESSES EMPLOYING INDICATOR LIGANDS

[75] Inventors: David Robert Bryant, South Charleston, W. Va.; Tak Wai Leung, Houston, Tex.

[73] Assignee: Union Carbide Chemicals & Plastics Technology Corporation, Danbury, Conn.

[21] Appl. No.: 757,741

[22] Filed: Nov. 26, 1996

Related U.S. Application Data

[60] Provisional application No. 60/008,289, and provisional application No. 60/008,763, and provisional application No. 60/008,284, and provisional application No. 60/008,286, filed on Dec. 6, 1995.

[51] Int. Cl.$^6$ ................................................ C07C 45/50
[52] U.S. Cl. ................................................ 568/454; 568/451
[58] Field of Search ................................ 568/454, 451

[56] References Cited

FOREIGN PATENT DOCUMENTS 0214622  3/1987  European Pat. Off. .

*Primary Examiner*—Gary Geist
*Assistant Examiner*—Sreeni Padmanabhan
*Attorney, Agent, or Firm*—Gerald L. Coon

[57] ABSTRACT

This invention relates to processes which comprise reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst, to produce one or more products. The sterically hindered organophosphorus ligands are useful as indicators of organopolyphosphite ligand depletion in said processes.

17 Claims, No Drawings

PROCESSES EMPLOYING INDICATOR LIGANDS

This application claims the benefit of provisional U.S. patent application Ser. Nos. 60/008289, 60/008763, 60/008284 and 60/008286, all filed Dec. 6, 1995, and all of which are incorporated herein by reference.

BRIEF SUMMARY OF THE INVENTION

1. Technical Field

This invention relates to processes employing a metal-organophosphorus ligand complex catalyst and, as indicators of organopolyphosphite ligand depletion in said processes, one or more sterically hindered organophosphorus ligands.

2. Background of the Invention

Organophosphine-promoted rhodium hydroformylation catalysts, especially triphenylphosphine promoted rhodium catalysts, have played important roles in the past and continue to play important roles in the production of aldehydes from terminal olefins.

The organophosphine ligands have several essential functions in the catalyst system. First, they moderate the chemical reactivity of rhodium. As a result, the rate of production of aldehyde the hydroformylation process is a function of the organophosphine ligand and its concentration. Furthermore, the selectivity of an organophosphine-promoted rhodium catalyst system is often dependent on the concentration of the ligand present. For example, the higher the triphenylphosphine concentration is, the more normal aldehyde product is produced.

A second function of the organophosphine ligand is to keep the precious rhodium in solution so that it will not be lost to precipitation or deposition to the reaction vessels. When the organophosphine ligand is bound to rhodium, the solubility of rhodium in organic solvents, including aldehydes, is increased. This increase in solubility of rhodium decreases the chance of rhodium being precipitated out of the reaction solution and becoming inactive and unrecoverable. Also, organophosphine ligands help prevent rhodium from forming large cluster compounds which are less soluble in organic solvent and are more likely to precipitate out of the reaction solution.

Recent advancements in hydroformylation catalyst technology include a new class of organophosphorus ligands called organopolyphosphites which have been shown to be superior in many aspects to organophosphines in promoting rhodium based catalysis. Some of the organopolyphosphite-promoted rhodium hydroformylation catalysts have been shown to be many times as active as the triphenylphosphine-promoted rhodium catalyst. There is one characteristic of the organopolyphosphite-promoted rhodium systems which differ from the organophosphine-promoted rhodium systems, especially from the triphenylphosphine-promoted rhodium system. While a stoichiometric amount of the organopolyphosphite to that of rhodium is required to produce a desirable catalyst system, the activity and selectivity of the organopolyphosphite-promoted rhodium catalyst are less dependent on the amount of organopolyphosphite beyond the stoichiometric amount.

Since organopolyphosphites are more difficult to synthesize, hence, they are more expensive. It is therefore not desirable to employ any excess organopolyphosphite than the required amount to the catalyst solution where it could undergo undesirable degradation reactions. Therefore, a practical hydroformylation catalyst system based on organopolyphosphite-promoted rhodium catalyst may have a much lower ligand concentration in contrast to an organophosphine-promoted system. As a result, a desirable amount of organopolyphosphite ligand to be employed would be the same molar concentration as that of the rhodium employed. In practice, however, it would mean a slight excess of the organopolyphosphite ligand to ensure that rhodium is not being short of the organopolyphosphite ligand and the catalyst system will behave as designed.

As mentioned above, one of the functions of a ligand in the catalyst system is to keep rhodium in solution and to prevent it from precipitating out of solution and becoming intractable. Since it is not chemically and economically desirable to employ organopolyphosphite ligands in the amounts that organophosphine ligands are employed in the corresponding hydroformylation system, there exists a risk of losing rhodium in the organopolyphosphite-promoted catalyst system which employs only the minimum amount of organopolyphosphite ligand required for rate and isomer ratio purposes. Conceivably, any phosphorus ligand can undergo reactions, expectedly or unexpectedly, by which it will be consumed. When this occurs in an organophosphine-promoted rhodium catalyst system, unless the reaction is extensive and drastic, the effect on the rhodium is minimal since there is a large amount of organophosphine ligand present to absorb any considerable amount of ligand loss. The rhodium would still be very much solubilized and protected from becoming intractable.

In contrast, if by any means that the organopolyphosphite ligand is consumed, the organopolyphosphite catalyst system in which only a minimum organopolyphosphite ligand required for operation is employed, would be at risk of losing rhodium to its intractable form. This is because the system does not have much excess ligand to lose before the molar ratio of organopolyphosphite ligand to rhodium falls below stoichiometric. Once that molar ratio is less than stoichiometric, rhodium is at risk of becoming intractable.

This invention provides a unique and highly desirable solution to this problem.

DISCLOSURE OF THE INVENTION

It has been discovered that certain sterically hindered organophosphorus ligands can be used as indicators of organopolyphosphite ligand depletion in chemical processes. The sterically hindered organophosphorus ligands are unique in that they can give indications that the organopolyphosphite concentration has reached a point which needs to be increased, and they can also serve to protect the metal, e.g., rhodium, from becoming intractable by helping to keep rhodium in solution when organopolyphosphite ligand concentration is depleted in chemical processes.

This invention relates in part to a process which comprises reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst, to produce one or more products, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

This invention also relates in part to an improved process which comprises (i) reacting in at least one reaction zone one or more reactants in the presence of a metal-organopolyphosphite ligand complex catalyst and optionally free organopolyphosphite ligand to produce a reaction product fluid comprising one or more products and (ii) separating in at least one separation zone or in said at least one reaction zone the one or more products from said reaction product fluid, the improvement comprising conducting said process in the presence of a sterically hindered organophosphorus ligand different from the organopolyphosphite ligand of said metal-organopolyphosphite ligand complex catalyst, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

This invention further relates in part to a method of monitoring organopolyphosphite ligand depletion in a process which comprises reacting one or more reactants in the presence of a metal-organopolyphosphite ligand complex catalyst and optionally free organopolyphosphite ligand to produce one or more products, which method comprises conducting said process in the presence of a sterically hindered organophosphorus ligand different from the organopolyphosphite ligand of said metal-organopolyphosphite ligand complex catalyst, in an amount sufficient to monitor said organopolyphosphite ligand depletion; wherein said sterically hindered organophosphorus ligand (i) has a coordination strength with respect to the metal of said metal-organopolyphosphite ligand complex catalyst less than the organopolyphsphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

This invention yet further relates in part to a reaction mixture comprising one or more products in which said reaction mixture is prepared by a process which comprises reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst, to produce said reaction mixture comprising one or more products, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

This invention also relates in part to a batchwise or continuously generated reaction mixture comprising, based on 100 percent of the weight of the reaction mixture and exclusive of any water present:

(1) greater than about 25, preferably greater than about 90, weight percent of one or more products;

(2) less than about 30, preferably less than about 10, weight percent of one or more reactants;

(3) less than about 10, preferably less than about 1, weight percent of a metal-organopolyphosphite ligand complex catalyst;

(4) less than about 10, preferably less than about 5, weight percent of a sterically hindered organophosphorus ligand different from the organopolyphosphite ligand of said metal-organopolyphosphite ligand complex catalyst; and (5) less than about 5, preferably less than about 1, weight percent of a metal-sterically hindered organophosphorus ligand complex catalyst;

wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

This invention further relates in part to a catalyst precursor composition comprising a metal-organopolyphosphite ligand complex catalyst and a sterically hindered organophosphorus ligand different from the organopolyphosphite ligand of said metal-organopolyphosphite ligand complex catalyst, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

DETAILED DESCRIPTION

General Processes

The processes of this invention may be asymmetric or non-asymmetric, the preferred processes being non-asymmetric, and may be conducted in any continuous or semi-continuous fashion and may involve any catalyst liquid and/or gas recycle operation desired. The particular processes for producing products from one or more reactants, as well as the reaction conditions and ingredients of the processes are not critical features of this invention. The processing techniques of this invention may correspond to any of the known processing techniques heretofore employed in conventional processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion. As used herein, the term "reaction product fluid" is contemplated to include, but not limited to, a reaction mixture containing an amount of any one or more of the following: (a) a metal-organopolyphosphite ligand complex catalyst, (b) free organopolyphosphite ligand, (c) one or more phosphorus acidic compounds formed in the reaction, (d) aldehyde product formed in the reaction, (e) unreacted reactants, and (f) an organic solubilizing agent for said metal-organopolyphosphite ligand complex catalyst and said free organopolyphosphite ligand. The reaction product fluid encompasses, but is not limited to, (a) the reaction medium in the reaction zone, (b) the reaction medium stream on its way to the separation zone, (c) the reaction medium in the separation zone, (d) the recycle stream between the separation zone and the reaction zone, (e) the reaction medium withdrawn from the reaction zone or separation zone for treatment in the acid removal zone, (f) the withdrawn reaction medium treated in the acid removal zone, (g) the treated reaction medium returned to the reaction zone or separation zone, and (h) reaction medium in external cooler.

This invention encompasses the carrying out of known conventional syntheses in a conventional fashion employing a metal-organopolyphosphite ligand complex catalyst and a sterically hindered organophosphorus ligand different from the organopolyphosphite ligand of said metal-organopolyphosphite ligand complex catalyst, in an amount sufficient to monitor organopolyphosphite ligand depletion in said conventional syntheses.

Illustrative processes include, for example, hydroformylation, hydroacylation (intramolecular an a intermolecular), hydrocyanation, hydroamidation, hydroesterification, aminolysis, alcoholysis, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-organopolyphosphite ligand complex catalyst. The most preferred processes include hydroformylation, hydrocyanation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organopolyphosphite ligand complex catalyst described herein. Alternatively, hydroxyaldehydes can be prepared by reacting an epoxide, carbon monoxide and hydrogen under hydroformylation conditions in the presence of a metal-organopolyphosphite ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-organopolyphosphite ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organopolyphosphite ligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-organopolyphosphite ligand complex catalyst described herein. A preferred hydrocyanation process involves reacting a nonconjugated acyclic aliphatic monoolefin, a monoolefin conjugated to an ester group, e.g., methyl pent-2-eneoate, or a monoolefin conjugated to a nitrile group, e.g., 3-pentenenitrile, with a source of hydrogen cyanide in the presence of a catalyst precursor composition comprising zero-valent nickel and a bidentate phosphite ligand to produce a terminal organonitrile, e.g., adiponitrile, alkyl 5-cyanovalerate or 3-(perfluoroalkyl) propionitrile. Preferably, the reaction is carried out in the presence of a Lewis acid promoter. Illustrative hydrocyanation processes are disclosed in U.S. Pat. No. 5,523,453 and WO 95/14659, the disclosures of which are incorporated herein by reference.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organopolyphosphite ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organopolyphosphite ligand complex catalyst described herein.

Aminolysis can be carried out in accordance with conventional procedures known in the art. For example, amines can be prepared by reacting an olefin with a primary or secondary amine under aminolysis conditions in the presence of a metal-organopolyphosphite ligand complex catalyst described herein.

Alcoholysis can be carried out in accordance with conventional procedures known in the art. For example, ethers can be prepared by reacting an olefin with an alcohol under alcoholysis conditions in the presence of a metal-organopolyphosphite ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organopolyphosphite ligand complex catalyst described herein.

Isomerization can be carried out in accordance with conventional procedures known in the art. For example, allylic alcohols can be isomerized under isomerization conditions to produce aldehydes in the presence of a metal-organopolyphosphite ligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-organopolyphosphite ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, intermolecular hydroacylation, hydrocyanation, hydroamidation, hydroesterfication, aminolysis, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Certain sterically hindered organophosphorus ligands have been found to be suitable ligands to use as indicators of organopolyphosphite ligand depletion in chemical processes. Since the desired indicator organophosphorus ligands are sterically hindered, they do not interfere with the organopolyphosphite ligand-promoted metal complex catalyst when one equivalent or more of the organopolyphosphite to metal is present. But when the organopolyphosphite is depleted to a concentration less than 1 equivalent to metal, these sterically hindered ligands provide a means for the metal to stay soluble, and not become intractable, by binding to the metal. Also, because of the ability of these sterically hindered organophosphorus ligands, e.g., certain organophosphine ligands and organophosphite ligands, to promote metal catalyzed processes at different rate and selectivity, the resulting catalyst system is able to give a significant indication when the organopolyphosphite is depleted below 1 equivalent to metal.

The superior characteristics of the organopolyphosphite promoted rhodium catalyst enable processes to produce desirable products while increasing the productivity of such processes. For example, because of the high activity of the organopolyphosphite-promoted rhodium catalysts, less precious rhodium metal is needed for the process leading to a lower investment and operating cost for the process.

Furthermore, in contrast to conventional organophosphine-promoted rhodium catalysts, organopolyphosphite-promoted rhodium catalysts require much less ligand to be present in the system to enable the system to produce aldehyde products with high normal-:branched aldehyde ratios. This aspect is a significant improvement over the organophosphine-promoted rhodium systems, both from a technical standpoint and an economic standpoint. There is no need to have a large excess of organopolyphosphite ligand which could occupy a substantial volume of the reactor. Since more catalyst volume would be available with the same reactor space, more aldehyde products can now be produced. Thus, efficiency is improved.

As mentioned above, organopolyphosphite ligands are much more difficult to make than triphenylphosphine ligands and, therefore, more expensive than triphenylphosphine ligands. Furthermore, unlike most organophosphines which are not very reactive with water, organopolyphosphites are more susceptible to hydrolysis especially under acidic conditions. The hydrolysis of the organopolyphosphites produces yet more acidic materials which further help the hydrolysis of the organopolyphosphite ligands. The result due to the loss of ligand in an organopolyphosphite promoted rhodium catalyst system can be very costly. Rhodium metal has a tendency to become intractable when the organophosphorus ligand is lacking. When rhodium becomes intractable, production of aldehyde is severely affected. To avoid any interruption in an organopolyphosphite-promoted process and to assure smooth operation, one must deal with potential problems with preventive measures.

This invention provides a particular preventive measure which is effective in performing two specific functions which largely help prevent the metal, e.g., rhodium, from becoming intractable. The two specific functions are: (1) to give indications that the organopolyphosphite concentration has reached a point which needs to be increased; and (2) to protect the metal, e.g., rhodium, from becoming intractable by helping to keep rhodium in solution.

The preventive measure as mentioned above relates to adding one or more certain sterically hindered organophosphorus ligands which can bind to the metal, e.g., rhodium, when the organophosphite ligand is depleted below the 1:1 molar ratio to metal. This added ligand will then keep the metal in solution. Furthermore, the sterically hindered organophosphorus ligand used for this preventive purpose desirably has a different characteristic with respect to its ability to influence the metal in the catalysis. The sterically hindered ligand chosen for this purpose will promote the metal catalyzed process at a different rate or, more importantly, with a different selectivity to the products, e.g., different normal:branched aldehyde ratios. Therefore, when the organopolyphosphite concentration is above the 1:1 molar ratio to metal, the metal catalyst system behaves as an organopolyphosphite-promoted metal system despite the presence of this added sterically hindered ligand. But when the organopolyphosphite concentration is less than a molar ratio of 1:1 to metal, the characteristic of the catalyst system changes. This change of the reaction rate and/or the change in selectivity of the process catalyst, e.g., different normal:branched aldehyde ratios, serves as a signal indicating that it is time to replenish the organopolyphosphite ligand.

Organopolyphosphite ligand-promoted rhodium catalysts have been shown to have many advantages over conventional triphenylphosphine ligand-promoted rhodium catalysts. Some of the organopolyphosphite ligands have been shown to be excellent activity promoters. More importantly, many of the organopolyphosphites have been shown to influence the selectivity of the rhodium catalyst system. For instance, the rhodium catalyst system using Ligand A in the examples below as a promoter was shown to be a much more active system for the hydroformylation of propylene than the conventional system using triphenylphosphine ligand as the promoter. At the same time, a much higher content of normal aldehyde than branched aldehyde was produced.

Furthermore, the normal:branched aldehyde ratio of the product is not a function of the organopolyphosphite to rhodium ratio as long as the organopolyphosphite to rhodium ratio is greater than 1. This is in contrast to the conventional triphenylphosphine ligand-promoted rhodium system where a certain triphenylphosphine to rhodium ratio must be maintained in order to get a desired normal:branched aldehyde ratio of the products.

Organopolyphosphites are expensive to produce. Therefore, it is desirable to employ the minimal amount of organopolyphosphite that is necessary to keep a metal catalyst to function properly in the desired manner so as to minimize the cost of ligand usage. Nevertheless, organopolyphosphites do undergo ligand degradation under catalysis conditions. It is well known that, without any ligand, the metal-ligand catalyst would deactivate quickly and the metal, e.g., rhodium, would become inactive and intractable.

The organopolyphosphite ligands useful in this invention contain two or more tertiary (trivalent) phosphorus atoms and include those ligands represented by formulas (VI) through (XII) below. The sterically hindered organophosphorus ligands useful as indicator ligands in this invention can be any of the organophosphine ligands and organophosphite ligands represented by formulas (I) through (XII) below, provided that the chosen sterically hindered organophosphorus ligand meets the criteria set forth herein.

Since one would like to use the minimal amount of organopolyphosphite and, at the same time, would not want to operate in a regime that would risk losing metal to its intractable form, it is therefore desirable to employ a method that would prevent the loss of rhodium without using a large excess of the organopolyphosphite ligand. It is also desirable to employ a method so that a warning signal can be detected that the organopolyphosphite ligand has degraded below stoichiometric and needs to be replenished. Such a method of indicating the need to replenish ligand is very important from the standpoint of process operations because it would avoid unnecessary shutdown or interruptions due to metal loss.

The sterically hindered organophosphorus ligands useful as indicator ligands in this invention (i) have a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, enable a reaction rate of at least 25 percent of the reaction rate provided by the organopolyphosphite ligand of said metal-organopolyphosphite ligand complex catalyst, (iii) optionally have a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, enable a normal:branched product isomer ratio lower than the normal:branched product isomer ratio provided by the organopolyphosphite ligand of said metal-organopolyphosphite ligand complex catalyst. The use of sterically hindered organophosphorus ligands as indicators of organopolyphosphite ligand depletion in hydroformylation processes employing a metal-organopolyphosphite ligand complex catalyst is disclosed in copending U.S. patent application Ser. No. 08/756,500 filed on an even date herewith, the disclosure of which is incorporated herein by reference.

As indicated above, the sterically hindered organophosphorus ligand of the metal-sterically hindered organophosphorus ligand complex catalyst provides a normal:branched product, e.g., aldehyde, isomer ratio lower than the normal:branched product, e.g., aldehyde, isomer ratio provided by the organopolyphosphite ligand of the metal-organopolyphosphite ligand complex catalyst. Preferably, the normal:branched product, e.g., aldehyde, isomer ratio provided by the sterically hindered organophosphorus ligand of the metal-sterically hindered organophosphorus ligand complex catalyst is no more than about 50 percent, more preferably no more than about 25 percent, of the normal:branched product, e.g., aldehyde, isomer ratio provided by the organopolyphosphite ligand of the metal-organopolyphosphite ligand complex catalyst.

In a preferred embodiment, the sterically hindered organophosphorus ligands useful in this invention as indicator ligands may include any of the organophosphorus ligands, e.g., organophosphine ligands and organophosphite ligands, represented by formulas (I) through (XII) below, provided that such sterically hindered organophosphorus ligands meet the criteria set forth herein. Preferred sterically hindered organophosphite ligands useful in this invention as indicator ligands include diorganophosphites and oxides, e.g., monoxides, of organopolyphosphites.

Illustrative sterically hindered organophosphorus ligands include, for example, any triphenylphosphine, any tricyclohexylphosphine, any cyclohexyl diphenylphosphine or dicyclohexyl phenylphosphine with at least one substituent group on the 2- or 6-position (ortho-position) of the cyclohexyl or phenyl ring of the phosphine. The general structures of illustrative sterically hindered organophosphorus ligands are depicted below (the X groups may be the same or different and represent any permissible substituents that impart steric hinderance, e.g., a substituted or unsubstituted monovalent hydrocarbon radical.

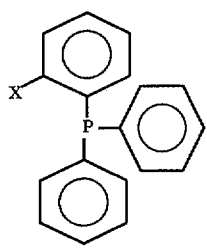
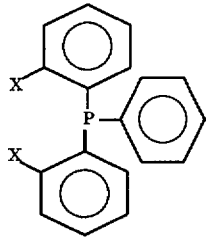
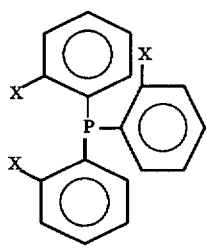
Triphenylphosphine with one, two or three substituent groups on any of the ortho positions of the phenyl rings.
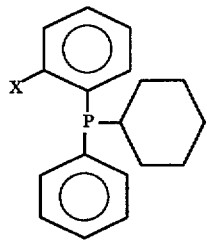
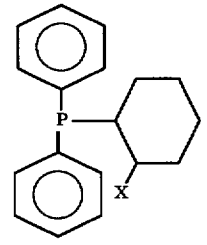
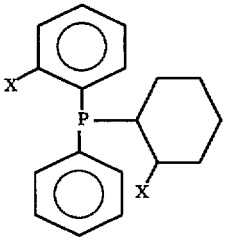
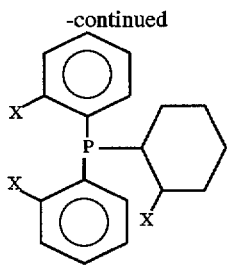
Cyclohexyl diphenylphosphine (CHDPP) with one, two or three substituent groups on any of the phenyl or cyclohexyl rings.
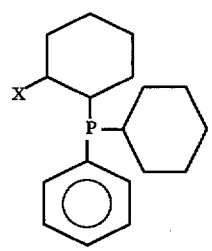
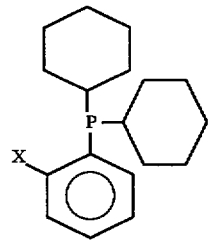
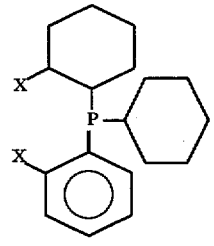
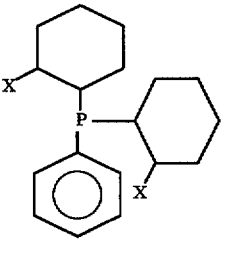
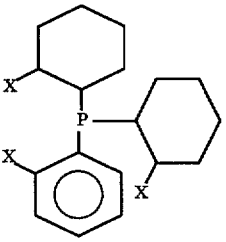

Diyclohexylphenylphosphine (DCHPP) with one, two or three substituent groups on any of the phenyl or cyclohexyl rings.

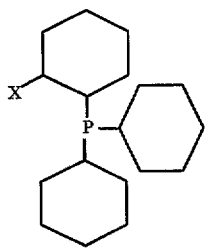

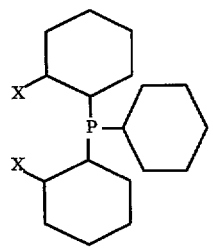

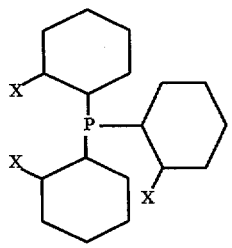

Tricyclohexylphosphine (TCHP) with one, two or three substituent groups on any of the cyclohexyl rings.

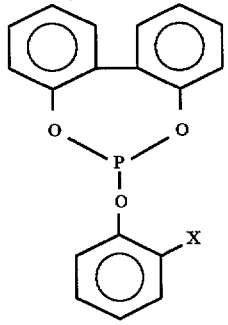

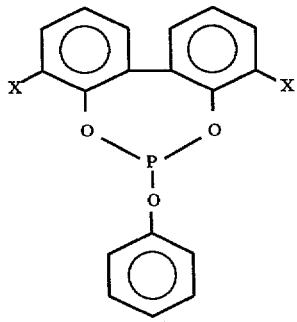

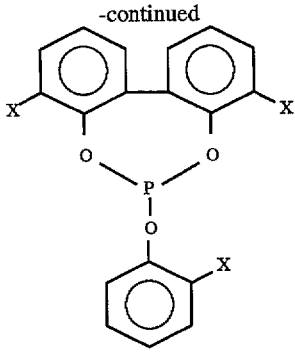

Diorganophosphite or an oxide of an organopolyphosphite, e.g., monoxide of a bisphosphite, with one, two or three substituent groups on any ortho positions of the rings.

The concentration of the sterically hindered organophosphorus ligands used as indicator ligands in the processes of this invention can be any amount greater than about 0.05 equivalent of the metal used. The upper limit depends on the solubility of the ligand. The preferred range is about 0.1 equivalent to about 10 equivalent of the metal employed.

The sterically hindered organophosphorus ligands useful in this invention as indicator ligands may deliberately be employed in the processes or formed in situ during said processes. Oxygen may deliberately (or not) be introduced into the reaction zone during the course of the reaction, e.g., a separate stream or through synthesis gas, to produce desired sterically hindered oxides, e.g., monoxides, of organopolyphosphite ligands.

Illustrative metal-organopolyphosphite ligand complex catalysts and metal-sterically hindered organophosphorus ligand complex catalysts employable in the processes encompassed by this invention are known in the art and include those disclosed in the below mentioned patents. In general such catalysts may be preformed or formed in situ as described in such references and consist essentially of metal in complex combination with an organopolyphosphite ligand or an organophosphorus ligand as the case may be. The active species may also contain carbon monoxide and/or hydrogen directly bonded to the metal.

The catalysts useful in the processes of this invention include a metal-organopolyphosphite ligand complex catalyst and a metal-sterically hindered organophosphorus ligand complex catalyst, both of which can be optically active or non-optically active. The permissible metals which make up the metal-organopolyphosphite ligand complexes and metal-sterically hindered organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 6 metals selected from chromium (Cr), molybdenum (Mo), tungsten (W) and mixtures thereof. Mixtures of metals from Groups 6, 8, 9 and 10 may also be used in this invention.

The permissible organopolyphosphite ligands which make up the metal-organopolyphosphite ligand complexes and free organopolyphosphite ligand include di-, tri- and higher polyorganophosphites. The permissible sterically hindered organophosphorus ligands which make up the metal-sterically hindered organophosphorus ligand complexes and free sterically hindered organophosphorus ligand include organophosphines and organophosphites which meet the criteria as described herein. Mixtures of such ligands may be employed if desired in the metal-organopolyphosphite ligand complex catalyst, the metal-sterically hindered organophosphorus ligand complex catalyst, any free organopolyphosphite ligand and/or any free sterically hindered organophosphorus ligand and such mixtures may be the same or different. This invention is not intended to be limited in any manner by the permissible organopolyphosphite ligands or mixtures thereof or the permissible sterically hindered organophosphorus ligands or mixtures thereof. It is to be noted that the successful practice of this invention does not depend and is not predicated on the exact structure of the metal-organopolyphosphite ligand complex species or the metal-sterically hindered organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organopolyphosphite ligand or sterically hindered organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organopolyphosphite ligands and sterically hindered organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2\!=\!CHCH_2$, $CH_3CH\!=\!CHCH_2$, $C_6H_5CN$, $CH_3CN$, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organopolyphosphite ligand complex catalyzed reactions that the active catalysts be free of halogen and sulfur directly bonded to the metal, although such may not be absolutely necessary.

The number of available coordination sites on such metals is well known in the art. Thus the catalytic species may comprise a complex catalyst mixture, in their monomeric, dimeric or higher nuclearity forms, which are preferably characterized by at least one organopolyphosphite-containing molecule complexed per one molecule of metal, e.g., rhodium. For instance, it is considered that the catalytic species of the preferred catalyst employed in a hydroformylation reaction may be complexed with carbon monoxide and hydrogen in addition to the organopolyphosphite ligands in view of the carbon monoxide and hydrogen gas employed by the hydroformylation reaction.

The organopolyphosphites that may serve as the ligand of the metal-organopolyphosphite ligand complex catalysts and/or free organopolyphosphite ligand, and the organophosphines and organophosphites that may serve as the sterically hindered ligand of the metal-sterically hindered organophosphorus ligand complex catalysts and/or free sterically hindered organophosphorus ligand of the processes of this invention may be of the achiral (optically inactive) or chiral (optically active) type and are well known in the art. Achiral organophosphorus ligands are preferred.

Among the organophosphines that may serve as the sterically hindered organophosphorus ligand of the metal-sterically hindered organophosphorus complex catalyst and/or free sterically hindered organophosphorus ligand of the reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, and bisphosphine mono oxides, and the like, all of which meet the criteria for sterically hindered organophosphorus ligands described herein. Of course any of the hydrocarbon radicals of such tertiary non-ionic and ionic organophosphines may be substituted if desired, with any suitable substituent that does not unduly adversely affect the desired result of the reaction. The sterically hindered organophosphine ligands employable in the reaction and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater, the most preferred hydrocarbon radical being phenyl, $(C_6H_5\!-\!)$. Illustrative substituent groups that may be present on the aryl radicals include, e.g., alkyl radicals, alkoxy radicals, silyl radicals such as $-\!Si(R^2)_3$; amino radicals such as $-\!N(R^2)_2$; acyl radicals such as $-\!C(O)R_2$; carboxy radicals such as $-\!C(O)OR_2$; acyloxy radicals such as $-\!OC(O)R_2$; amido radicals such as $-\!C(O)N(R^2)_2$ and $-\!N(R_2)C(O)R_2$; ionic radicals such as $-\!SO_3M$ wherein M represents inorganic or organic cation; sulfonyl radicals such as $-\!SO_2R_2$; ether radicals such as $-\!OR^2$; sulfinyl radicals such as $-\!SOR^2$; sulfenyl radicals such as $-\!SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as $-\!N(R^2)_2$, each $R^2$ taken together can also represent a divalent bridging group that forms a heterocyclic radical with the nitrogen atom and in amido substituents such as $C(O)N(R_2)_2$ and $-\!N(R^2)C(O)R^2$ each $-\!R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl; tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphosphines, e.g., of (tri-m-sulfophenyl)phosphine and of (m-sulfophenyl)diphenylphosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749 and 4,861,918, the disclosures of which are incorporated herein by reference.

Among the organophosphites that may serve as the sterically hindered organophosphorus ligand of the metal-sterically hindered organophosphorus complex catalyst and/or free sterically hindered organophosphorus ligand of the reaction mixture starting materials are monoorganophosphites, diorganophosphites, triorganophosphites and organopolyphosphites, all of which meet the criteria for sterically hindered organophosphorus ligands described herein. Preferred sterically hindered organophosphites include, for example, diorganophosphites, oxides of organopolyphosphites, e.g., monoxides of bisphosphites, and the like. The sterically hindered organophosphite ligands employable in this invention and/or methods for their preparation are known in the art.

Among the organopolyphosphites that may serve as the organopolyphosphite ligand of the metal-organopolyphosphite ligand complex catalyst and/or free organopolyphosphite ligand of the reaction mixture starting materials are organopolyphosphite ligands that contain two or more tertiary (trivalent) phosphorus atoms and include those ligands represented by formulas (VI) through (XII) below. The organopolyphosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

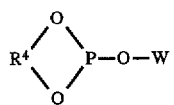
(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

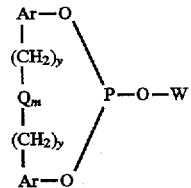
(IV)

wherein W is as defined above, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^6-$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

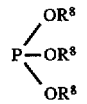
(V)

wherein each $R^8$ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for $R^1$ in formula (I). Illustrative triorganophosphites include, for example, dialkylaryl phosphites, alkyldiaryl phosphites, triaryl phosphites, and the like, such as, for example, tri-(2,6-diisopropylphenyl) phosphite, tri-(2,6-di-t-butylphenyl) phosphite, tri-(2-t-butyl-4-methoxyphenyl) phosphite, and the like. The most preferred triorganophosphite is tri-(2-t-butyl-4-methoxyphenyl) phosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

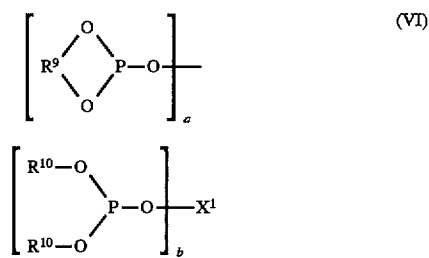

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361; 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

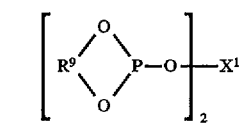

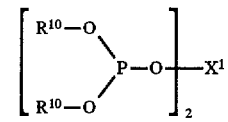

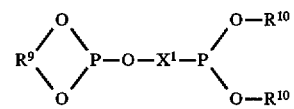

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

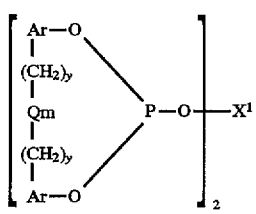

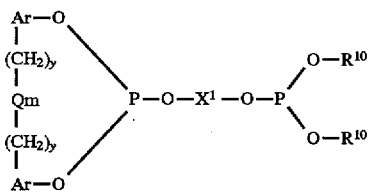

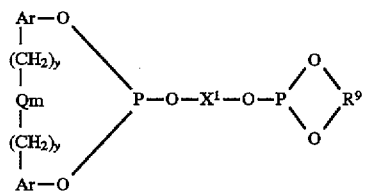

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by $-(CH_2)_y-(Q)_m-(CH_2)_y-$ is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (II) to (XII) may be an ionic phosphite, i.e., may contain one or more ionic moieties selected from the group consisting of:

$SO_3M$ wherein M represents inorganic or organic cation, $PO_3M$ wherein M represents inorganic or organic cation, $N(R^{11})_3X^2$ wherein each $R^{11}$ is the same or different and represents a hydrocarbon radical containing from 1 to 30 carbon atoms, e.g., alkyl, aryl, alkaryl, aralkyl, and cycloalkyl radicals, and $X^2$ represents inorganic or organic union, $CO_2M$ wherein M represents inorganic or organic cation, as described, for example, in U.S. Pat. Nos. 5,059,710; 5,113,022 5,114,473; 5,449,653; and European Patent Application Publication No. 435,084, the disclosures of which are incorporated herein by reference. Thus, if desired, such organophosphite ligands may contain from 1 to 3 such ionic moieties, while it is preferred that only one such ionic moiety be substituted on any given aryl moiety in the organophosphite ligand when the ligand contains more than one such ionic moiety. As suitable counter-ions, M and $X^2$, for the anionic moieties of the ionic organophosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation and quaternary ammonium cations, phosphonium cations, arsonium cations and iminium cations. Suitable anionic atoms of radicals include, for example, sulfate, carbonate, phosphate, chloride, acetate, oxalate and the like.

Of course any of the $R^3$, $R^4$, $R^8$, $R^9$, $R^{10}$, $X^1$, $X^2$, W, Q and Ar radicals of such non-ionic and ionic organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as $-Si(R^{12})_3$; amino radicals such as $-N(R^{12})_2$; phosphine radicals such as $-aryl-P(R^{12})_2$; acyl radicals such as $-C(O)R^{12}$; acyloxy radicals such as $-OC(O)R^{12}$; amido radicals such as $-CON(R^{12})_2$ and $-N(R^{12})COR^{12}$; sulfonyl radicals such as $-SO_2R^{12}$; alkoxy radicals such as $-OR^{12}$; sulfinyl radicals such as $-SOR^{12}$; sulfenyl radicals such as $-SR^{12}$; phosphonyl radicals such as $-P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as $-N(R^{12})_2$ each $R^{12}$ taken together can also represent a divalent bridging group that forms a heterocyclic radical with the nitrogen atom, and in amido substituents such as $-C(O)N(R^{12})_2$ and $-N(R^{12})COR^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-buryl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, $-OCH_2CH_2OCH_3$, $-(OCH_2CH_2)_2OCH_3$, $-(OCH_2CH_2)_3OCH_3$, and the like; aryloxy radicals such as phenoxy and the like; as well as silyl radicals such as $-Si(CH_3)_3$, $-Si(OCH_3)_3$, $-Si(C_3H_7)_3$, and the like; amino radicals such as $-NH_2$, $-N(CH_3)_2$, $-NHCH_3$, $-NH(C_2H_5)$, and the like; arylphosphine radicals such as $-P(C_6H_5)_2$, and the like; acyl radicals such as $-C(O)CH_3$, $-C(O)C_2H_5$, $-C(O)C_6H_5$, and the like; carbonyloxy radicals such as $-C(O)OCH_3$ and the like; oxycarbonyl radicals such as $-O(CO)C_6H_5$, and the like; amido radicals such as $-CONH_2$, $-CON(CH_3)_2$, $-NHC(O)CH_3$, and the like; sulfonyl radicals such as $-S(O)_2C_2H_5$ and the like; sulfinyl radicals such as $-S(O)CH_3$ and the like; sulfenyl radicals such as $-SCH_3$, $-SC_2H_5$, $-SC_6H_5$, and the like; phosphonyl radicals such as $-P(O)(C_6H_5)_2$, $-P(O)(CH_3)_2$, $-P(O)(C_2H_5)_2$, $-P(O)(C_3H_7)_2$, $-P(O)(C_4H_9)_2$, $-P(O)(C_6H_{13})_2$, $-P(O)CH_3(C_6H_5)$, $-P(O)(H)(C_6H_5)$, and the like.

Specific illustrative examples of organophosphite ligands include the following:

2-t-butyl-4-methoxyphenyl(3,3'-di-t-butyl-5,5'-dimethoxy-1,1'-biphenyl-2,2'-diyl)phosphite having the formula:

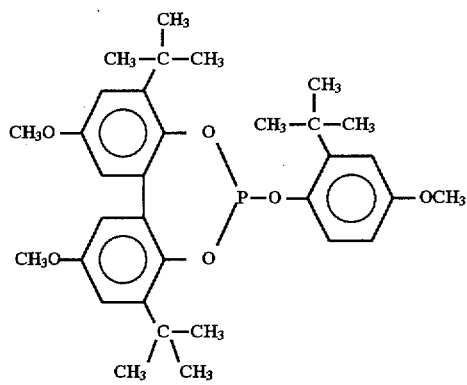

Ligand A methyl(3,3'-di-t-butyl-5,5'-dimethoxy-1,1'-biphenyl-2,2'-diyl)phosphite having the formula:

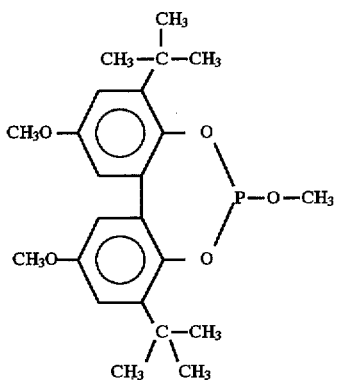

Ligand B 6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

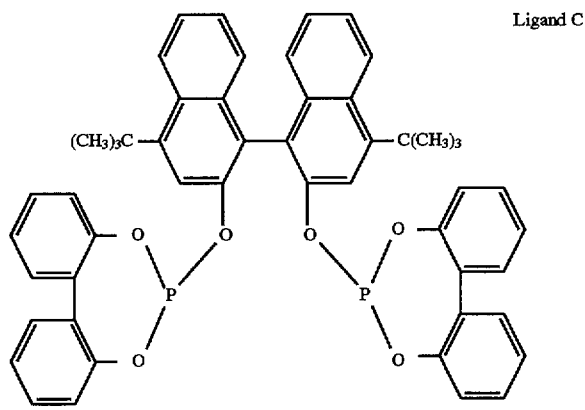

Ligand C 6,6'-[[3,3'-bis(1,1-dimethylethyl)-5,5'-dimethoxy-[1,1'-biphenyl]-2,2'-diyl]bis(oxy)]bis-dibenzo[d,f][1,3,2] dioxaphosphepin having the formula:

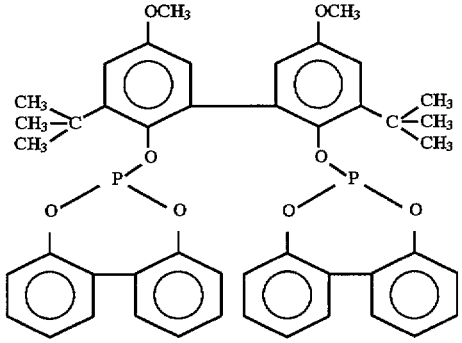

Ligand D 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

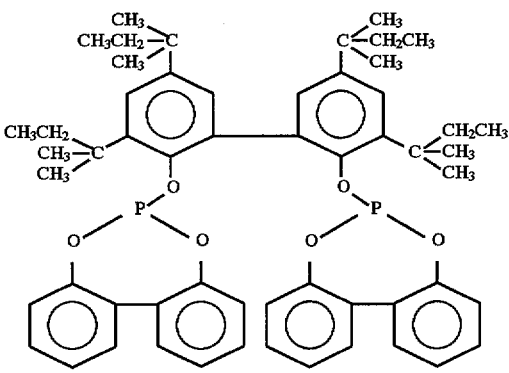

Ligand E 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

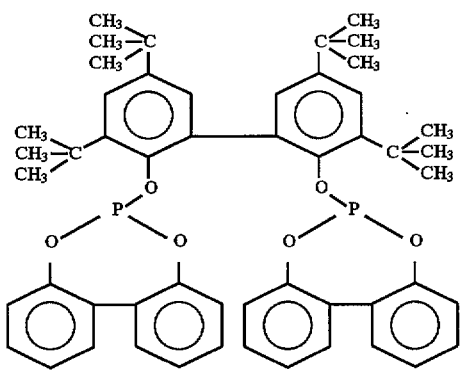

Ligand F (2R,4R)-di[2,2'-(3,3',5,5'-tetrakis-tert-amyl-1,1'-biphenyl)]-2,4-pentyldiphosphite having the formula:

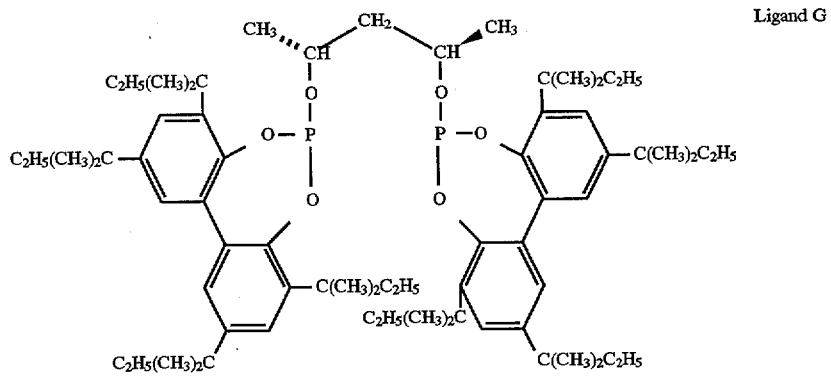
Ligand G
(2R,4R)-di[2,2'-(3,3',5,5'-tetrakis-tert-butyl-1,1'-biphenyl)]-2,4-pentyldiphosphite having the formula:
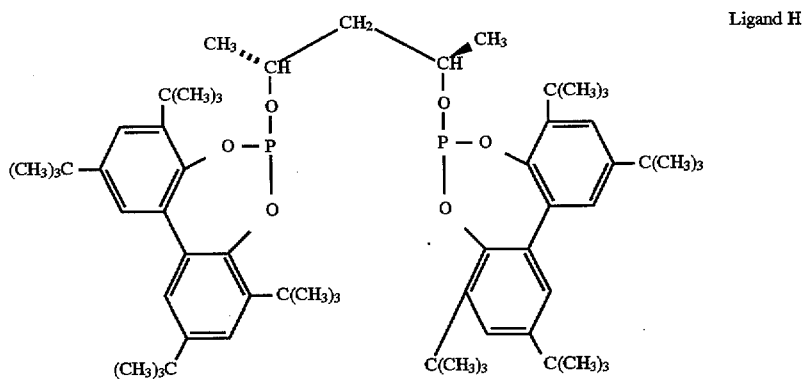
Ligand H
(2R,4R)-di[2,2'-(3,3'-di-amyl-5,5'-dimethoxy-1,1'-biphenyl)]- 2,4-pentyldiphosphite having the formula:
Ligand I
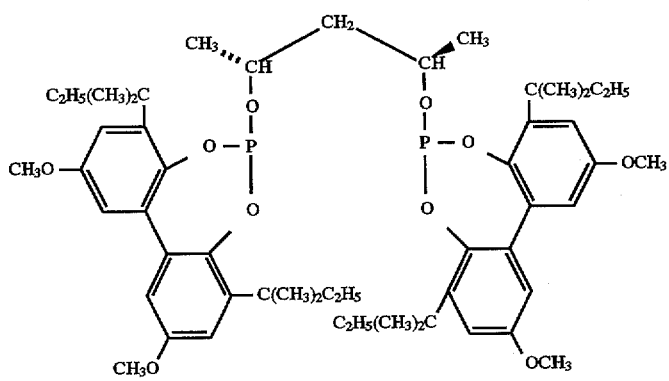
(2R,4R)-di[2,2'-(3,3'-di-tert-butyl-5,5'-dimethyl-1,1'-biphenyl)]-2,4-pentyldiphosphite having the formula:

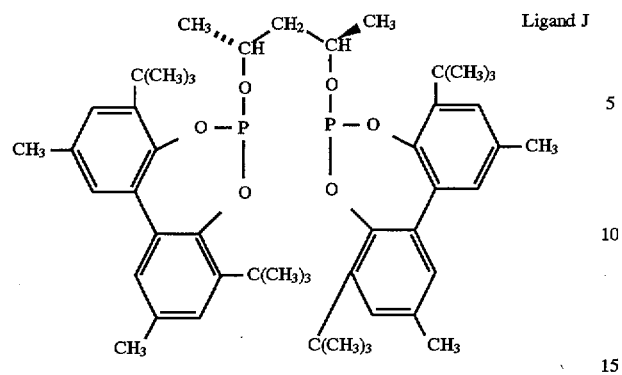
(2R,4R)-di[2,2'-(3,3'-di-tert-butyl-5,5'-diethoxy-1,1'-biphenyl)]-2,4-pentyldiphosphite having the formula:
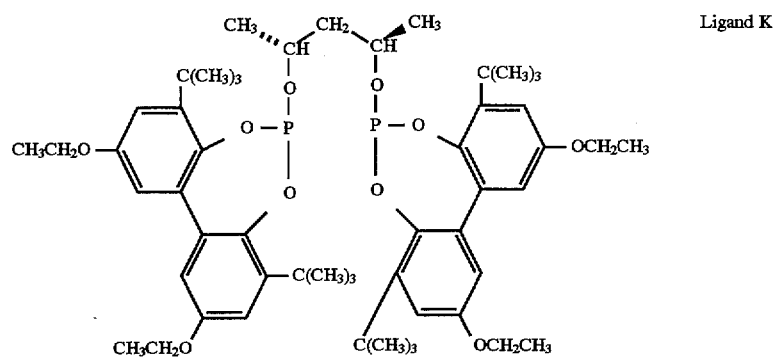
(2R,4R)-di[2,2'-(3,3'-di-tert-butyl-5,5'-diethyl-1,1'-biphenyl)]-2,4-pentyldiphosphite having the formula:
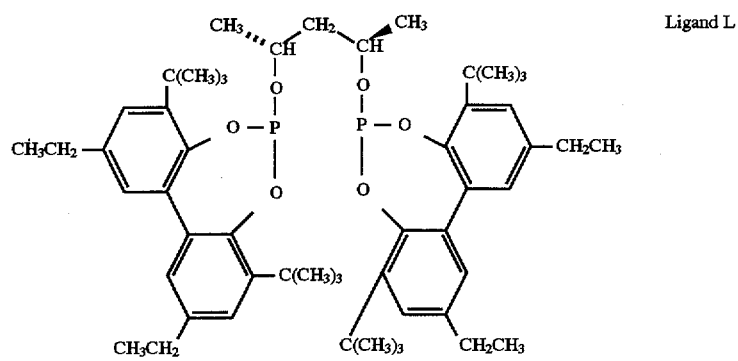
(2R,4R)-di[2,2'-(3,3'-di-tert-butyl-5,5'-dimethoxy-1,1'-biphenyl)]-2,4-pentyldiphosphite having the formula:

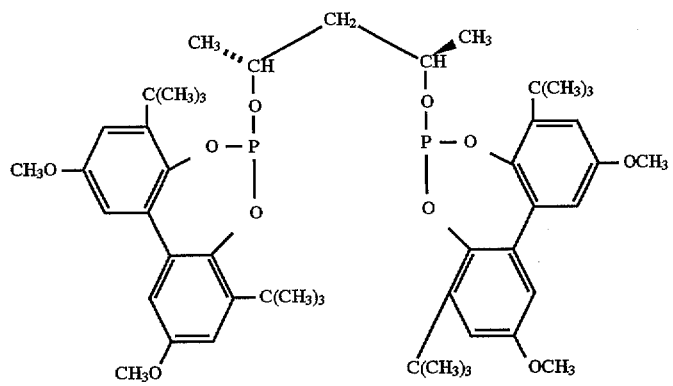

Ligand M

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

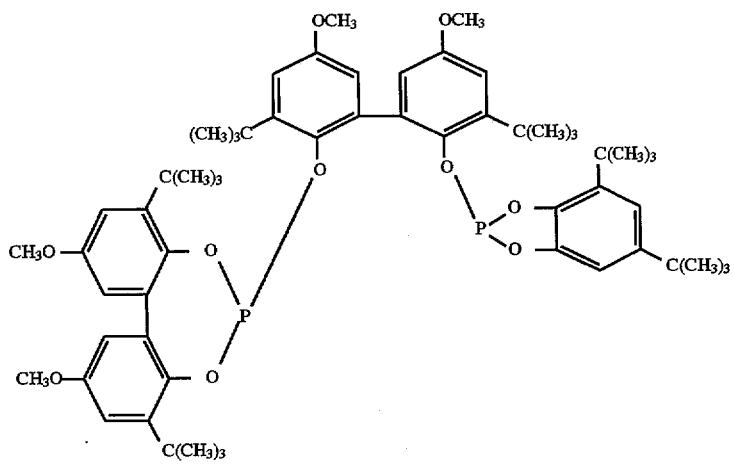

Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

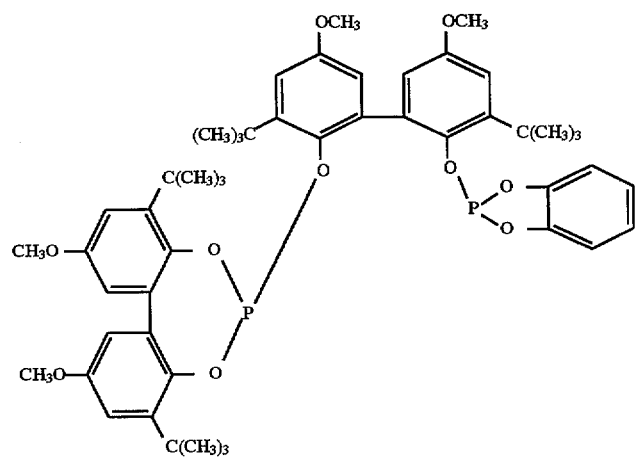

Ligand O

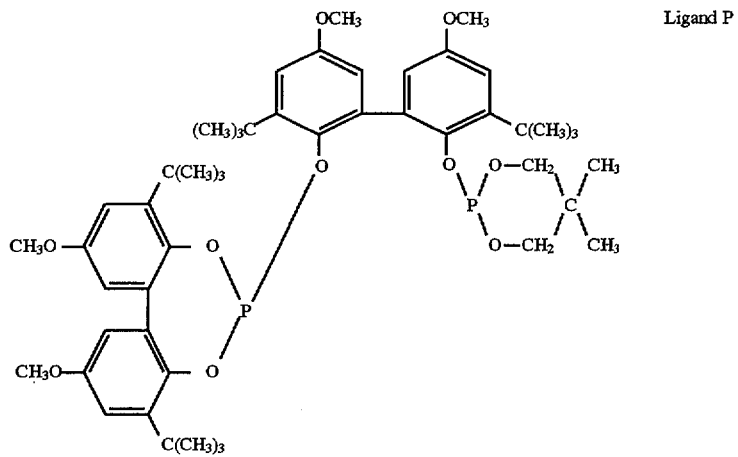

Ligand P

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

3-methoxy-1,3-cyclohexamethylene tetrakis[3,6-bis(1,1-dimethylethyl)-2-naphthalenyl]ester of phosphorous acid having the formula:

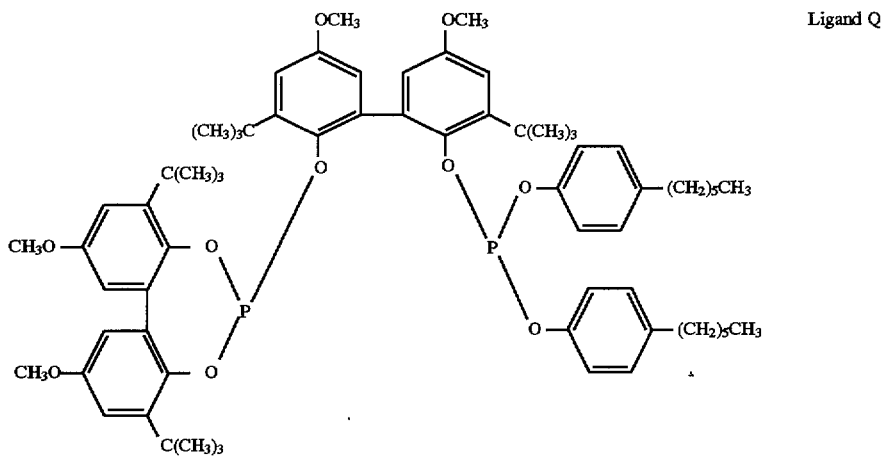

Ligand Q

2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

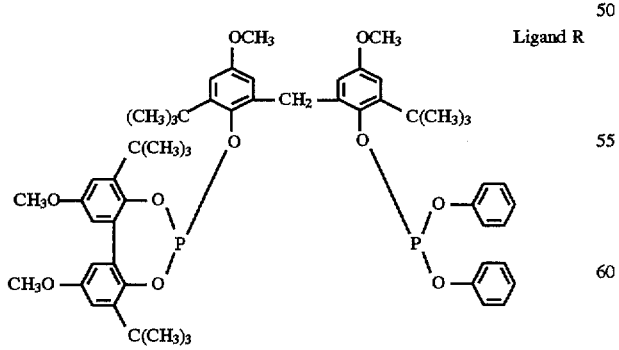

Ligand R

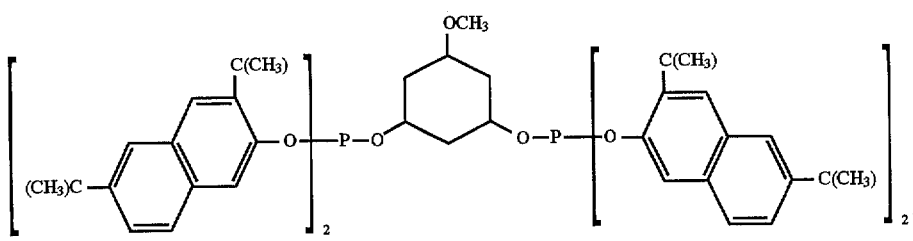

Ligand S 2,5-bis(1,1-dimethylethyl)-1,4-phenylene tetrakis[2,4-bis(1,1-dimethylethyl)phenyl]ester of phosphorous acid having the formula:

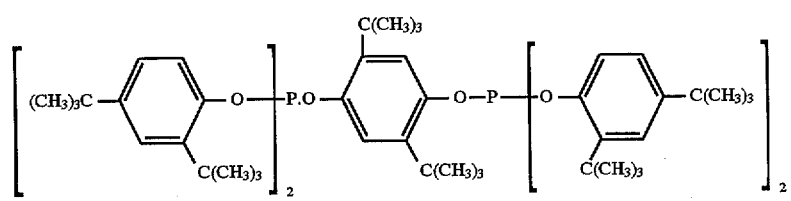

Ligand T methylenedi-2,1-phenylene tetrakis[2,4-bis(1,1-dimethylethyl)phenyl]ester of phosphorous acid having the formula:

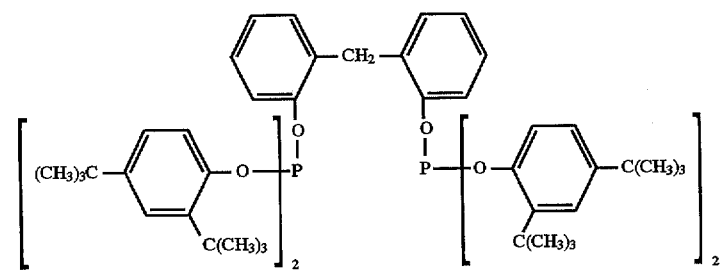

Ligand U

[1,1'-biphenyl]-2,2'-diyl tetrakis[2-(1,1-dimethylethyl)-4-methoxyphenyl]ester of phosphorous acid having the formula:

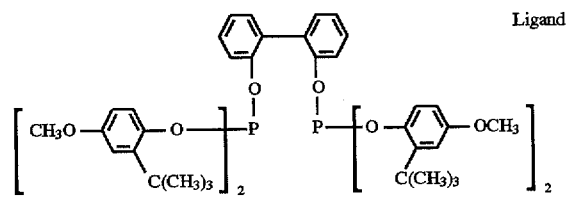

Ligand V

As noted above, the metal-organopolyphosphite ligand complex catalysts employable in this invention may be formed by methods known in the art. The metal-organopolyphosphite ligand complex catalysts may be in homogeneous or heterogeneous form. For instance, preformed rhodium hydrido-carbonyl-organopolyphosphite ligand catalysts may be prepared and introduced into the reaction mixture of a particular process. More preferably, the metal-organopolyphosphite ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organopolyphosphite ligand for the in situ formation of the active catalyst. In a preferred embodiment of this invention, rhodium dicarbonyl acetylacetonate is employed as a rhodium precursor and reacted in the presence of a solvent with the organopolyphosphite ligand to form a catalytic rhodium-organopolyphosphite ligand complex precursor which is introduced into the reaction zone along with excess (free) organopolyphosphite ligand for the in situ formation of the active catalyst. In any event, it is sufficient for the purpose of this invention that carbon monoxide, hydrogen and organopolyphosphite compound are all ligands that are capable of being complexed with the metal and that an active metal-organopolyphosphite ligand catalyst is present in the reaction mixture under the conditions used in the hydroformylation reaction.

More particularly, a catalyst precursor composition can be formed consisting essentially of a solubilized metal-organopolyphosphite ligand complex precursor catalyst, an organic solvent and free organopolyphosphite ligand. Such precursor compositions may be prepared by forming a solution of a rhodium starting material, such as a rhodium oxide, hydride, carbonyl or salt, e.g., a nitrate, which may or may not be in complex combination with a organopolyphosphite ligand as defined herein. Any suitable rhodium starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organopolyphosphite ligand rhodium carbonyl hydrides. Carbonyl and organopolyphosphite ligands, if not already complexed with the initial rhodium, may be complexed to the rhodium either prior to or in situ during the process.

By way of illustration, the preferred catalyst precursor composition of this invention consists essentially of a solubilized rhodium carbonyl organopolyphosphite ligand complex precursor catalyst, a solvent and optionally free organopolyphosphite Ligand prepared by forming a solution of rhodium dicarbonyl acetylacetonate, an organic solvent and a organopolyphosphite ligand as defined herein. The organopolyphosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organopolyphosphite ligand complex precursor are soluble can be employed. The amounts of rhodium complex catalyst precursor, organic solvent and organopolyphosphite ligand, as well as their preferred embodiments present in such catalyst precursor compositions may obviously correspond to those amounts employable in the processes of this invention. Experience has shown that the acetylacetonate ligand of the precursor catalyst is replaced after the process, e.g., hydroformylation, has begun with a different ligand, e.g., hydrogen, carbon monoxide or organopolyphosphite ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor rhodium and hydroformylation start-up. The metal-sterically hindered organophosphorus ligand complex catalysts can be prepared in the same manner as the metal-organopolyphosphite ligand complex catalysts described above.

Accordingly, the metal-organopolyphosphite ligand complex catalysts used in the processes of this invention consists essentially oft he metal complexed with carbon monoxide, i.e., hydroformylation, and an organopolyphosphite ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organopolyphosphite ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organopolyphosphite ligand complex catalyst may be present as a result of being ligands Sound to a precursor catalyst and/or as a result of in situ formation, e.g., due to the hydrogen and carbon monoxide gases employed in hydroformylation process of this invention.

As noted above, the organopolyphosphite ligands can be employed as both the ligand of the metal-organopolyphosphite ligand complex catalyst, as well as, the free organopolyphosphite ligand that can be present in the reaction medium of the processes of this invention. In addition, it is to be understood that while the organopolyphosphite ligand of the metal-organopolyphosphite ligand complex catalyst and any excess free organopolyphosphite ligand preferably present in a given process of this invention are normally the same type of ligand, different types of organopolyphosphite ligands, as well as, mixtures of two or more different organopolyphosphite ligands may be employed for each purpose in any given process, if desired.

The amount of metal-organopolyphosphite ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organopolyphosphite ligand complex catalysts, the processes of this invention and especially the hydroformylation process can be carried out in the presence of free organopolyphosphite ligand. While the processes of this invention may be carried out in any excess amount of free organopolyphosphite ligand desired, the employment of free organopolyphosphite ligand may not be absolutely necessary. Accordingly, in general, amounts of ligand of from about 1.1 or less to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

As indicated above, the catalysts may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (i.e. alumina, silica, titania, or zirconia) carbon, or ion exchange resins. The catalyst may be supported on, or intercalated inside the pores of, a zeolite, glass or clay; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The metal, e.g., rhodium, catalyst may be attached to a thin film or membrane support, such as cellulose acetate or polyphenylenesulfone, as described in for example J. Mol. Cat. 1990, 63, 213–221.

The metal, e.g., rhodium, catalyst may be attached to an insoluble polymeric support through an organophosphorus-containing ligand, such as a phosphite, incorporated into the polymer. The supported catalyst is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire process and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

More preferably, the hydroformylation reaction is carried out in the slurry phase due to the high boiling points of the products, and to avoid decomposition of the aldehyde products. The catalyst may then be separated from the product mixture, for example, by filtration or decantation. The reaction product fluid may contain a heterogeneous metal-organopolyphosphite ligand complex catalyst, e.g., slurry, or at least a portion of the reaction product fluid may contact a fixed heterogeneous metal-organopolyphosphite ligand complex catalyst during the particular process. In an embodiment of this invention, the metal-organopolyphosphite ligand complex catalyst may be slurried in the reaction product fluid.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about $-80°$ C. or less to about $500°$ C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention and preferably the hydroformylation process may be conducted in the presence of an organic solvent for the metal-organopolyphosphite ligand complex catalyst. The solvent may also contain dissolved water up to the saturation limit. Depending on the particular catalyst and reactants employed, suitable organic solvents include, for example, alcohols, alkanes, alkenes, alkynes, ethers, aldehydes, ketones, esters, amides, mines, aromatics and the like. Any suitable solvent which does not unduly adversely interfere with the intended processes can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that amount sufficient to provide the reaction medium with the particular metal concentration desired for a given process. In general, the amount of solvent when employed may range from about 5 percent by weight up to about 99 percent by weight or more based on the total weight of the reaction mixture starting materials.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The desired products of this invention may be recovered in any conventional manner and one or more separators or separation zones may be employed in any given process to recover the desired reaction product from its crude reaction product fluid. Suitable separation methods include, for example, solvent extraction, crystallization, distillation, vaporization, wiped film evaporation, falling film evaporation and the like. It may be desired to remove the products from the crude reaction mixture as they are formed through the use of trapping agents as described in published Patent Cooperation Treaty Patent Application WO 88/08835. A preferred method for separating the product mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

The processes of this invention may involve reacting one or more reactants in the presence of a metal-organopolyphosphite ligand complex catalyst to produce a reaction product fluid comprising one or more products, wherein said process is conducted at a free organopolyphosphite ligand concentration sufficient to prevent and/or lessen hydrolytic degradation of the organopolyphosphite ligand and deactivation of the metal-organopolyphosphite ligand complex catalyst. See, for example, copending U.S. patent application Ser. Nos. 08/756,789 and (D-17687), both filed on an even date herewith, the disclosures of which are incorporated herein by reference.

The processes of this invention may be carried out using, for example, a fixed bed reactor, a fluid bed reactor, a continuous stirred tank reactor (CSTR) or a slurry reactor. The optimism size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discrete vessels. The at least one separation zone employed in this invention may be a single vessel or may comprise two or more discrete vessels. The at least one buffer treatment zone employed in this invention may be a single vessel or may comprise two or more discrete vessels. It should be understood that the reaction zone(s) and separation zone(s) employed herein may exist in the same vessel or in different vessels. For example, reactive separation techniques such as reactive distillation, reactive membrane separation and the like may occur in the reaction zone(s).

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydrofonnylation processes useful in this invention may be carried out in a multistaged reactor such as described, for example, in copending U.S. patent application Ser. No. 08/757,742, filed on an even date herewith, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a Single vessel is a cost effective way of using the reactor vessel volume. It significantly reduces the number of vessels that otherwise would be required to achieve the same results. Fewer vessels reduces the overall capital required and maintenance concerns with separate vessels and agitators.

Hydroformylation Processes

A preferred process useful in this invention is hydroformylation. Illustrative metal-organopolyphosphite ligand complex catalyzed hydroformylation processes include such processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques of this invention may correspond to any known processing techniques. Preferred process are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organopolyphosphite ligand complex catalyst in a liquid medium that also contains an organic solvent for the catalyst and ligand. Preferably free organopolyphosphite ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194 and copending U.S. patent application Ser. No. 08/430,790, filed May 5, 1995, the disclosures of which are incorporated herein by reference, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syn gas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydrofonnylation reaction mixtures employable herein includes any mixture derived from any corresponding hydroformylation process that contains at least some amount of five different main ingredients or components, i.e., the aldehyde product, a metal-organopolyphosphite ligand complex catalyst, free organopolyphosphite ligand, free sterically hindered organophosphorus ligand, and an organic solubilizing agent for said catalyst and said free ligands, said ingredients corresponding to those employed and/or produced by the hydrofonnylation process from whence the hydrofonnylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

The substituted or unsubstituted olefin reactants that may be employed in the hydroformylation processes (and other suitable processes) of this invention include both optically active (prochiral and chiral) and non-optically active (achiral) olefinic unsaturated compounds containing from 2 to 40, preferably 4 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more ethylenic unsaturated groups, and of course, mixtures of two or more different olefinic unsaturated compounds may be employed as the starting material if desired. For example, commercial alpla olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, mixed butenes, e.g., Raffinate I and II. Further such olefinic unsaturated compounds and the corresponding products derived therefrom may also contain one or more groups or substituents which do not unduly adversely affect the processes of this invention such as described, for example, in U.S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 4 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-penterie, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alphamethyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Illustrative prochiral and chiral olefins useful in the asymmetric hydroformylation processes (and other asymmetric processes) that can be employed to produce enantiomeric product mixtures that may be encompassed by in this invention include those represented by the formula:

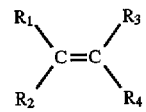

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, vitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, vitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation processes (and other asymmetric processes) of this invention include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360, 938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-organopolyphosphite ligand complex catalyst as described hereinabove. The hydroformylation catalysts may be in homogeneous or heterogeneous form during the reaction and/or during the product separation. Of course mixtures Of such catalysts can also be employed if desired. The amount of metal-organopolyphosphite ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 350 parts per million of metal, e.g., rhodium.

In addition to the metal-organopolyphosphite ligand complex catalyst, free organopolyphosphite ligand (i.e., ligand that is not complexed with the metal) may also be present in the hydroformylation reaction medium. The free organopolyphosphite ligand may correspond to any of the above-defined organopolyphosphite ligands employable herein. It is preferred that the free organopolyphosphite ligand be the same as the organopolyphosphite ligand of the metal-organopolyphosphite ligand complex catalyst employed. However, such ligands need not be the same in any given process. The hydroformylation process of this invention may involve from about 0.1 moles or less to about 100 moles or higher, of free organopolyphosphite ligand per mole of metal in the hydrofonnylation reaction medium. Preferably the hydrofonnylation process of this invention is carried out in the presence of from about 1 to about 50 moles of organopolyphosphite ligand, and more preferably for organopolyphosphites from about 1.1 to about 4 moles of organopolyphosphite ligand, per mole of metal present in the reaction medium; said amounts of organopolyphosphite Ligand being the sum of both the amount of organopolyphosphite ligand that is bound (complexed) to the metal present and the amount of free (non-complexed) organopolyphosphite ligand present. Since it is more preferred to produce non-optically active aldehydes by hydroformylating achiral olefins, the more preferred organopolyphosphite Ligands are achiral type organopolyphosphite ligands, especially those encompassed by Formula (VI) above, and more preferably those of Formulas (VII) and (X) above. Of course, if desired, make-up or additional organopolyphosphite ligand can be supplied to the reaction medium of the hydroformylation process at any time and in any suitable manner, e.g. to maintain a predetermined level of free ligand in the reaction medium.

The concentration of the sterically hindered organophosphorus ligands used as indicator ligands in the processes of this invention can be any amount greater than about 0.05 equivalent of the metal used. The upper limit depends on the solubility of the ligand. The preferred range is about 0.1 equivalent to about 10 equivalent of the metal employed.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 500 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 120° C. are preferred for all types of olefinic starting materials. Of course it is to be understood that when non-optically active aldehyde products are desired, achiral type olefin starting materials and organopolyphosphite ligands are employed and when optically active aldehyde products are desired prochiral or chiral type olefin starting materials and organopolyphosphite ligands are employed. Of course, it is to be also understood that the hydroformylation reaction conditions employed will be governed by the type of aldehyde product desired.

The hydroformylation processes encompassed by this invention are also conducted in the presence of an organic solvent for the metal-organopolyphosphite ligand complex catalyst and free organopolyphosphite ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl)propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organopolyphosphite ligand complex catalyst, free organopolyphosphite ligand and free sterically hindered organophosphorus ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-organopolyphosphite complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination, of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, phase separation, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction product fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reaction zone as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organopolyphosphite ligand and reaction products. When an alpha-mono-olefin reactant is also employed, the aldehyde derivative thereof can also be separated by the above methods.

More particularly, distillation and separation of the desired aldehyde product from the metal-organopolyphosphite complex catalyst containing reaction product fluid may take place at any suitable temperature desired. In general, it is recommended that such distillation take place at relatively low temperatures, such as below 150° C., and more preferably at a temperature in the range of from about 50° C. to about 140° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reaction zone to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

In the following examples, accelerated testing procedures have been employed for demonstrating this invention. The testing procedures allows one to obtain meaningful results in a much shorter and manageable period of time than under normal hydroformylation procedures.

Certain of the following examples are provided to further illustrate this invention.

GLOSSARY

For purposes of the examples below, the following terms have the indicated meaning:

Rate—The rate of production of aldehyde from olefin.
N/B ratio—The mole ratio of the normal (linear) aldehyde product to iso (branched) aldehyde product.
Syn gas—Synthesis gas (mixture of hydrogen and carbon monoxide).
ppm—Parts per million parts by weight.
Ligand Structures:

Ligand Structures:

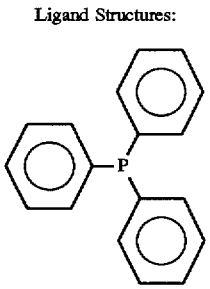

Triphenylphosphine,
(TPP)

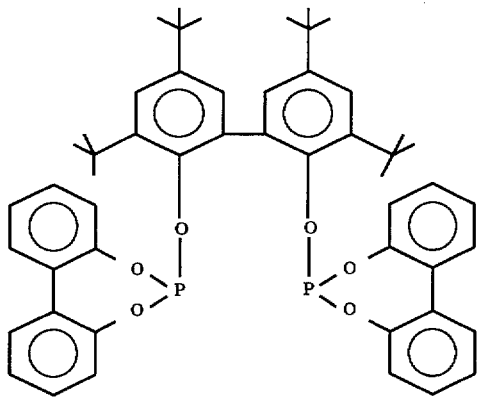

Ligand A: 6,6'-[[3,3', 5,5'-tetrakis(1,1-dimethylethyl)-[1,1'-biphenyl]-2,2'-diyl]bis(oxy)]bis-dibenzo[d,f][1,3,2]dioxaphosphepin.
Ligand A as used in the examples is the same ligand as Ligand D depicted in the specification.

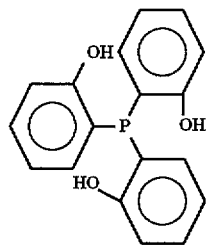

Ligand B:
Tris(2-hydroxyphenyl)-
phosphine
T-2-HOPP

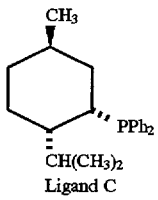

Ligand C

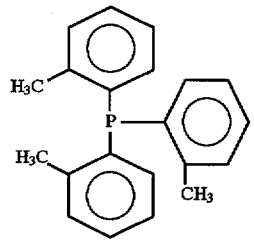

Ligand D
Tri-2-methylphenylphosphine
T-2-MEPP

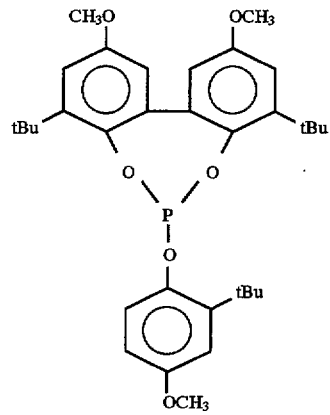

Ligand E

-continued

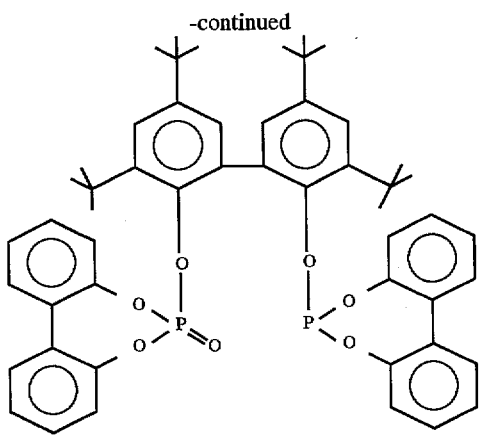

Ligand F
Monoxide of Ligand A

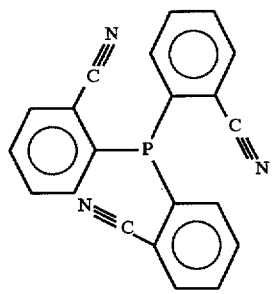

Ligand G
Tris(2-cyanophenyl)phosphine
T-2-CNPP

EXAMPLE 1

This example illustrates the following: (1) that T-2-HOPP (Ligand B) can keep rhodium in a soluble state and at the same time hydroformylating an olefin to aldehydes; and (2) aldehyde products with low N/B ratio were obtained with only the indicator ligand present but products with high N/B ratio were obtained once when stoichiometric or more than stoichiometric amount of Ligand A to rhodium was added to the system.

A solution of 200 ppm rhodium in the form of rhodium dicarbonyl acetylacetonate, and 2.0 equivalents (to rhodium) of T-2-HOPP were charged into a single pass reactor employed in a continuous single pass hydroformylation process directed to hydroformylating propylene. The catalyst activity, measured in rate/propylene partial pressure, was profiled as a function of time. The isomer ratio of the normal to branched aldehyde products was obtained at the same time by gas chromatography. After 3 days, 2.0 equivalents of Ligand A was added. The monitoring of the catalyst activity and ratio of aldehyde products were continued. Table 1 shows the results.

TABLE 1

| Days in operation | Rate, g-mol/liter | N/B normal to branched product ratio |
|---|---|---|
| 0.5 | 0.004 | 0.6 |
| 1.6 | 0.001 | 0.7 |
| 2.5 | 0.001 | 0.7 |
| 3.5 | 1.465 | 18.4 |
| 4.6 | 1.433 | 26.9 |
| 5.5 | 1.305 | 29.0 |
| 6.5 | 1.13 | 29.9 |
| 7.0 | 0.985 | 30.9 |

Table 1. Hydroformylation data showing that the indicator ligand T-2-HOPP is capable of promoting hydroformylation and keeping rhodium in solution. Upon the addition of Ligand A to the catalyst, the system behaved as a rhodium/Ligand A catalyst.

EXAMPLE 2

This example is to show that NMDPP (Ligand C) can keep rhodium in solution in the absence of Ligand A. It also showed that when Ligand A is present, the system behaves as a rhodium/Ligand A system despite the presence of Ligand C.

A solution of 200 ppm rhodium in the form of rhodium dicarbonylacetylacetonate, and 2.0 equivalents (to rhodium) of Ligand C were charged into a single pass reactor employed in a continuous single pass hydroformylation process directed to hydroformylating propylene. The catalyst activity, measured in rate/propylene partial pressure, was profiled as a function of time. The isomer ratio of the normal to branched aldehyde products was obtained at the same time by gas chromatography. After 3 days, 2.0 eq. of Ligand A was added. The monitoring of the catalyst activity and ratio of aldehyde products were continued. Table 2 shows the results.

TABLE 2

| Days in operation | Rate, g-mol/liter | N/B normal to branched product ratio |
|---|---|---|
| 0.5 | 0.23 | 1.2 |
| 0.9 | 0.19 | 1.3 |
| 1.5 | 0.16 | 1.3 |
| 2.0 | 0.17 | 1.3 |
| 2.5 | 0.18 | 1.3 |
| 2.8 | 0.15 | 1.5 |
| 3.2* | 0.95 | 11.1 |
| 3.8 | 0.88 | 16.2 |
| 4.0 | 0.87 | 18.6 |
| 4.5 | 1.04 | 19.8 |
| 5.0 | 1.29 | 15.8 |
| 5.4 | 1.26 | 16.4 |
| 6.0 | 1.30 | 16.0 |
| 6.5 | 1.30 | 16.5 |
| 7.0 | 1.24 | 18.4 |

*Ligand A was added at day 3.0.

Table 2. Hydroformylation data showing that the indicator ligand NMDPP (Ligand C), is capable of promoting hydroformylation and keeping rhodium in solution. Upon the addition of Ligand A to the catalyst, the system behaved as a rhodium/Ligand A catalyst.

EXAMPLE 3

This example shows that Ligand D (T-2-MEPP) can keep rhodium in solution in the absence of Ligand A. It also shows that when Ligand A is present, the system behaves as a rhodium/Ligand A system despite the presence of Ligand D.

A solution of 200 ppm rhodium in the form of rhodium dicarbonyl acetylacetonate, and 2.0 equivalents (to rhodium) of Ligand D were charged into a single pass reactor employed in a continuous single pass hydroformylation process directed to hydroformylating propylene. The catalyst activity, measured in rate/propylene partial pressure, was profiled as a function of time. The isomer ratio of the normal to branched aldehyde products was obtained at the same time by gas chromatography. After 2 days, 2.0 equivalents of Ligand A was added. The monitoring of the catalyst activity and ratio of aldehyde products were continued. Table 3 shows the results.

TABLE 3

| Days in operation | Rate, g-mol/liter | N/B normal to branched product ratio |
| --- | --- | --- |
| 0.50 | 0.004 | 0.4 |
| 1.5 | 0.001 | 0.7 |
| 2.6 | 0.001 | 0.7 |
| 3.5 | 1.01 | 14.8 |
| 4.5 | 1.00 | 14.1 |
| 5.5 | 0.95 | 12.9 |
| 6.5 | 0.86 | 12.6 |
| 7.0 | 0.84 | 12.8 |

*Ligand A added in day 2.0

Table 3. Hydroformylation data showing that Ligand D (T-2-MEPP) is capable of promoting hydroformylation and keeping rhodium in solution. Upon the addition of Ligand A to the catalyst, the system behaved as a rhodium/Ligand A catalyst.

EXAMPLE 4

This example shows that Ligand E can keep rhodium in solution in the absence of Ligand A. It also shows that when Ligand A is present, the system behaves as a rhodium/Ligand A system despite the presence of Ligand E.

A solution of 200 ppm rhodium in the form of rhodium dicarbonyl acetylacetonate, and 2.0 equivalents (to rhodium) of Ligand E were charged into a single pass reactor employed in a continuous single pass hydroformylation process directed to hydroformylating propylene. The catalyst activity, measured in rate/propylene partial pressure, was profiled as a function of time. The isomer ratio of the normal to branched aldehyde products was obtained at the same time by gas chromatography. After 2 days, 2.0 equivalents of Ligand A was added. The monitoring of the catalyst activity and ratio of aldehyde products were continued. Table 4 shows the results.

TABLE 4

| Days in operation | Rate, g-mol/liter | N/B normal to branched product ratio |
| --- | --- | --- |
| 0.5 | 0.41 | 0.8 |
| 0.8 | 0.32 | 0.9 |
| 1.1 | 0.25 | 1.0 |
| 1.5 | 0.23 | 0.9 |
| 1.8 | 0.21 | 0.9 |
| 2.5* | 0.64 | 23 |
| 2.9 | 0.87 | 27 |
| 3.5 | 0.81 | 31 |

TABLE 4-continued

| Days in operation | Rate, g-mol/liter | N/B normal to branched product ratio |
| --- | --- | --- |
| 4.0 | 0.74 | 27 |
| 4.5 | 0.75 | 32 |

*Ligand A added at day 2.0

Table 4. Hydroformylation data showing that Ligand E is capable of promoting hydroformylation and keeping rhodium in solution. Upon the addition of Ligand A to the catalyst, the system behaved as a rhodium/Ligand A catalyst.

EXAMPLE 5

This example shows that Ligand F can keep rhodium in solution in the absence of Ligand A. It also showed that when Ligand A is present, the system behaved as a rhodium/Ligand A system despite the presence of Ligand F.

A solution of 200 ppm rhodium in the form of rhodium dicarbonyl acetylacetonate, and 2.0 equivalents (to rhodium) of Ligand F were charged into a single pass reactor employed in a continuous single pass hydroformylation process directed to hydroformylating propylene. The catalyst activity, measured in rate/propylene partial pressure, was profiled as a function of time. The isomer ratio of the normal to branched aldehyde products was obtained at the same time by gas chromatography. After 2 days, 2.0 equivalents of Ligand A was added. The monitoring of the catalyst activity and ratio of aldehyde of products were continued. Table 5 shows the results.

TABLE 5

| Days in operation | Rate, g-mol/liter | N/B normal to branched product ratio |
| --- | --- | --- |
| 0.5 | 1.78 | 1.1 |
| 0.8 | 1.63 | 1.1 |
| 1.2 | 1.69 | 1.2 |
| 1.5 | 1.70 | 1.2 |
| 1.8 | 1.75 | 1.2 |
| 2.5* | 1.35 | 24 |
| 2.8 | 1.18 | 33 |
| 3.5 | 1.16 | 35 |
| 4.1 | 1.07 | 35 |
| 4.5 | 1.14 | 38 |

*Ligand A added in day 2.0

Table 5. Hydroformylation data showing that Ligand F is capable of promoting hydroformylation and keeping rhodium in solution. Upon the addition of Ligand A to the catalyst, the system behaved as a rhodium/Ligand A catalyst.

EXAMPLE 6

This example demonstrates that rhodium/Ligand A is a catalyst system producing high normal to branched aldehyde products. When Ligand A concentration is below stoichiometric to rhodium, Ligand E helps keep rhodium soluble and the resulting system produces low normal to branched product, a difference which can serve as a signal for the need of more Ligand A. Addition of more Ligand A completely converted the system to a rhodium/Ligand A system.

A tetraglyme solution of 200 ppm rhodium in the form of rhodium dicarbonyl acetylacetonate and 2.0 equivalents (to rhodium) of Ligand E was charged into a 50 cubic centimeter autoclave reactor equipped with temperature controls. The system was purged with nitrogen once and syn gas twice. It was then pressurized with 100 psi of 1:1:1 propylene: carbon monoxide: hydrogen gas mixture. After the system reached 70° C., the rate of gas uptake was measured to obtain the reaction rate. A sample of the reaction solution was taken to be analyzed so as to obtain the normal to branched aldehyde products.

After the rate measurement and the sampling were done, a 0.25 equivalent of Ligand A was added. The rate measurement and product sampling were again carried out. The procedure was again repeated. The results of the experiment are summarized in Table 6.

TABLE 6

| Indicator Ligand (# of eq.) | # of eq. of Ligand A added | Catalyst Activity | Cumulative N/B |
|---|---|---|---|
| Ligand E (3.0) | 0.00 | 2.0 | 0.95 |
| Ligand E (3.0) | 0.25 | 1.2 | 2.8 |
| Ligand E (3.0) | 0.50 | 2.0 | 4.7 |
| Ligand E (3.0) | 1.0 | 1.8 | 7.0 |
| Ligand E (3.0) | 2.0 | 1.7 | 9.1 |

Table 6. Mini-reactor data showing that Ligand E is a good indicator ligand as the N/B ratio of the products of hydroformylation are substantially different with and without Ligand A present in the system.

EXAMPLE 7

This example demonstrates that rhodium/Ligand A is a catalyst system producing high normal to branched aldehyde products. When Ligand A concentration is below stoichiometric to rhodium, Ligand F helps keep rhodium soluble and the resulting system produces low normal to branched product, a difference which can serve as a signal for the need of more Ligand A. Addition of more Ligand A completely converted the system to a rhodium/Ligand A system.

A tetraglyme solution of 200 ppm rhodium in the form of rhodium dicarbonyl acetylacetonate and 2.0 equivalents (to rhodium) of Ligand F was charged into a 50 cubic centimeter autoclave reactor equipped with temperature controls. The system was purged with nitrogen once and syn gas twice. It was then pressurized with 100 psi of 1:1:1 propylene: carbon monoxide: hydrogen gas mixture. After the system reached 70° C., the rate of gas uptake was measured to obtain the reaction rate. A sample of the reaction solution was taken to be analyzed so as to obtain the normal to branched aldehyde products.

After the rate measurement and the sampling were done, a 0.25 equivalents of Ligand A was added. The rate measurement and product sampling were again carried out. The procedure was again repeated. The results of the experiment are summarized in Table 7.

TABLE 7

| Indicator Ligand (# of eq.) | # of eq. of Ligand A added | Catalyst Activity | Cumulative N/B |
|---|---|---|---|
| Ligand F (3.0) | 0.00 | 0.97 | 1.2 |
| Ligand F (3.0) | 0.25 | 1.0 | 1.7 |

TABLE 7-continued

| Indicator Ligand (# of eq.) | # of eq. of Ligand A added | Catalyst Activity | Cumulative N/B |
|---|---|---|---|
| Ligand F (3.0) | 0.50 | 1.2 | 24 |
| Ligand F (3.0) | 1.0 | 1.2 | 28 |
| Ligand F (3.0) | 2.0 | 1.1 | 32 |

Table 7. Mini-reactor data showing that Ligand F is a good indicator ligand as the N/B ratio of the products of hydroformylation are substantially different with and without Ligand A present in the system.

EXAMPLE 8

This example demonstrates the ability of the Ligand B (T-2-HOPP) to protect rhodium from becoming intractable in case Ligand A is depleted completely.

To each of two separate Fisher-Porter Pressure bottles, 25 milliliters of a solution containing 300 ppm of rhodium and 0.24% of Ligand A (1.0 equivalents to rhodium) using a 50:50 mixture of n-butyraldehyde/tetraglyme as solvent. To one of the bottles, 2.0 equivalents of Ligand B were added. Both bottles were then sealed under an atmosphere of syn gas and heated to a temperature of 125° C. They were examined periodically. After 48 hours, a dark precipitate began to be observable in the Sample without the Ligand B. After 96 hours, a significant amount of metallic gray precipitate came out of solution in the sample without the Ligand B. On the other hand, there were no precipitate in the sample with the Ligand B charged.

EXAMPLE 9

This example demonstrates the ability of ligand C (NMDPP) to protect rhodium from becoming intractable in case Ligand A is depleted completely.

To each of two separate Fisher-Porter Pressure bottles, 25 milliliters of a solution containing 300 ppm of rhodium and 0.24% of Ligand A (1.0 equivalent to rhodium) using a 50:50 mixture of n-butyraldehyde/tetraglyme as solvent. To one of the bottles, 2.0 equivalents of Ligand C were added. Both bottles were then sealed under an atmosphere of syn gas and heated to a temperature of 125° C. They were examined periodically. After 48 hours, a dark precipitate began to be observable in the sample without the ligand C. After 96 hours, a significant amount of metallic gray precipitate came out of solution in the sample without the Ligand C. On the other hand, there were no precipitate in the sample with the Ligand C charged.

EXAMPLE 10

This example demonstrates the ability of Ligand G (T-2-CNPP) to protect rhodium from becoming intractable in case Ligand A is depleted completely.

To each of two separate Fisher-Porter Pressure bottles, 25 milliliters of a solution containing 300 ppm of rhodium and 0.24% of Ligand A (1.0 equivalent to rhodium) using a 50:50 mixture of n-butyraldehyde/tetraglyme as solvent. To one of the bottles, 2.0 equivalents of Ligand G were added. Both bottles were then sealed under an atmosphere of syn gas and heated to a temperature of 125° C. They were examined periodically. After 48 hours, a dark precipitate began to be observable in the sample without the Ligand G. After 96 hours, a significant amount of metallic gray precipitate came out of solution in the sample without the Ligand G. On the other hand, there were no precipitate in the sample with the Ligand G charged.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process which comprises reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst sufficient to give indications that the organopolyphosphite concentration has reached a point which needs to be increased, to produce one or more products, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

2. An improved process which comprises (i) reacting in at least one reaction zone one or more reactants in the presence of a metal-organopolyphosphite ligand complex catalyst and optionally free organopolyphosphite ligand to produce a reaction product fluid comprising one or more products and (ii) separating in at least one separation zone or in said at least one reaction zone the one or more products from said reaction product fluid, the improvement comprising conducting said process in the presence of a sterically hindered organophosphorus ligand different from the organopolyphosphite ligand of said metal-organopolyphosphite ligand complex catalyst in an amount sufficient to give indications that the organopolyphosphite concentration has reached a point which needs to be increased, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

3. A method of monitoring organopolyphosphite ligand depletion in a process which comprises reacting one or more reactants in the presence of a metal-organopolyphosphite ligand complex catalyst and optionally free organopolyphosphite ligand to produce one or more products, which method comprises conducting said process in the presence of a sterically hindered organophosphorus ligand different from the organopolyphosphite ligand of said metal-organopolyphosphite ligand complex catalyst, in an amount sufficient to monitor said organopolyphosphite ligand depletion; wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metalosterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

4. A reaction mixture comprising one or more products in which said reaction mixture is prepared by a process which comprises reacting one or more reactants in the presence of a metal-organopolyphosphite ligand complex catalyst and optionally free organopolyphosphite ligand, and an amount of a sterically hindered organophosphorus ligand different from the organopolyphosphite ligand of said metal-organopolyphosphite ligand complex catalyst sufficient to give indications that the or ganopolyphosphite concentration has reached a point which needs to be increased, to produce said reaction mixture comprising one or more products, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

5. A batchwise or continuously generated reaction mixture comprising, based on 100 percent of the weight of the reaction mixture and exclusive of any water present:

(1) greater than about 25, preferably greater than about 90, weight percent of one or more products;

(2) less than about 30, preferably less than about 10, weight percent of one or more reactants;

(3) less than about 10, preferably less than about 1, weight percent of a metal-organopolyphosphite ligand complex catalyst;

(4) less than about 10, preferably less than about 5, weight percent of a sterically hindered organophosphorus ligand different from the organopolyphosphite ligand of said metal-organopolyphosphite ligand complex catalyst; and (5) less than about 5, preferably less than about 1, weight percent of a metal-sterically hindered organophosphorus ligand complex catalyst;

wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphate ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

6. A catalyst precursor composition comprising a metal-organopolyphosphite ligand complex catalyst and a sterically hindered organophosphorus ligand different from the organopolyphsphite ligand Of said metal-organopolyphosphite ligand complex catalyst, wherein said sterically hindered organophosphorus ligand (i) has a coordination strength with respect to the metal of said metal-organopolyphosphite ligand complex catalyst less than the organopolyphosphite ligand of said metal-organopolyphosphite ligand complex catalyst, (ii) when complexed with the metal to form a metal-sterically hindered organophosphorus ligand complex catalyst, provides a reaction rate of at least 25 percent of the reaction rate provided by the organopolyphosphite ligand of said metal-organopolyphosphite ligand complex catalyst, (iii) optionally has a coordination strength with respect to the metal of said metal-organopolyphosphite ligand complex catalyst greater than carbon monoxide, and (iv) optionally when complexed with the metal to form a metal-sterically hindered organophosphorus ligand complex catalyst, provides a normal:branched product isomer ratio lower than the normal:branched product isomer ratio provided by the organopolyphosphite ligand of said metal-organopolyphosphite ligand complex catalyst.

7. The process of claim 1 which comprises a hydroformylation, hydroacylation (intramolecular and intermolecular), hydrocyanation, hydroamidation, hydroesterification, aminolysis, alcoholysis, carbonylation, isomerization or transfer hydrogenation process.

8. The process of claim 1 wherein said metal-organopolyphosphite ligand complex catalyst is homogeneous or heterogeneous.

9. The process of claim 1 wherein said process is carried out in the presence of from about 1.1 to about 4 moles of organopolyphosphite ligand per mole of metal present in the reaction medium.

10. The process of claim 1 wherein said sterically hindered organophosphorus ligand is present in an amount greater than about 0.05 equivalents of the metal employed.

11. The process of claim 1 wherein said metal-organopolyphosphite ligand complex catalyst comprises rhodium complexed with an organopolyphosphite ligand represented by the formula:

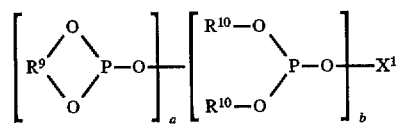

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

12. The process of claim 1 wherein said metal-organopolyphosphite ligand complex catalyst comprises rhodium complexed with an organopolyphosphite ligand having the formula selected from:

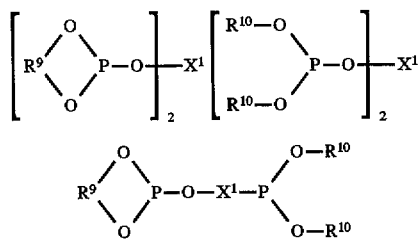

wherein $X^1$ represents a substituted or unsubstituted divalent hydrocarbon bridging radical containing from 2 to 40 carbon atoms, each $R^9$ is the same or different and represents a divalent hydrocarbon radical containing from 4 to 40 carbon atoms, and each $R^{10}$ is the same or different and represents a substituted or unsubstituted monovalent hydrocarbon radical containing from 1 to 24 carbon atoms.

13. The process of claim 1 wherein said metal-organopolyphosphite ligand complex catalyst comprises rhodium complexed with an organopolyphosphite ligand having the formula selected from:

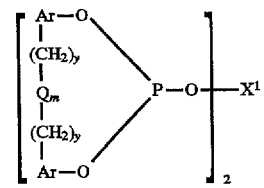

-continued

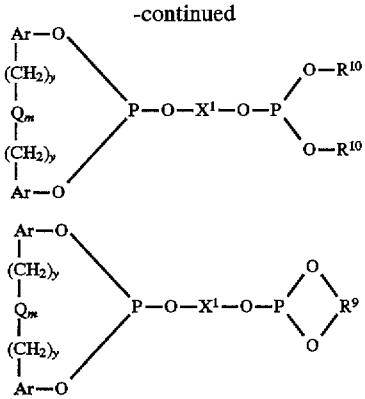

wherein $X^1$ represents a substituted or unsubstituted divalent hydrocarbon bridging radical containing from 2 to 40 carbon atoms, $R^9$ is a divalent hydrocarbon radical containing from 4 to 40 carbon atoms, each $R^{10}$ is the same or different and represents a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from i to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

14. The process of claim 1 wherein said metal-sterically hindered organophosphorus ligand complex catalyst comprises rhodium complexed with a sterically hindered organophosphorus ligand having the formula selected from:

(i) a triorganophosphine ligand represented by the formula:

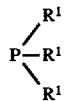

wherein $R^1$ is the same or different and represents a substituted or unsubstituted monovalent hydrocarbon radical containing from 1 to 24 carbon atoms or greater;

(ii) a monoorganophosphite represented by the formula:

wherein $R^3$ represents a substituted or unsubstituted trivalent hydrocarbon radical containing from 4 to 40 carbon atoms or greater;

(iii) a diorganophosphite represented by the formula:

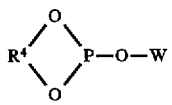

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and represents a substituted or unsubstituted monovalent hydrocarbon radical; and (v) an oxide of an organopolyphosphite represented by the formula:

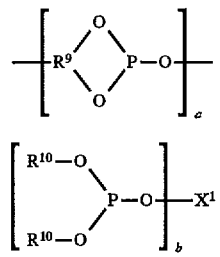

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

15. The process of claim 1 wherein said sterically hindered organophosphorus ligand comprises a sterically hindered organophosphine or organophosphite ligand.

16. The process of claim 15 wherein said sterically hindered organophosphine ligand comprises a substituted triphenylphosphine, a substituted tricyclohexylphosphine, a substituted cyclohexyl diphenylphosphine, or a substituted dicyclohexyl phenylphosphine.

17. The process of claim 15 wherein said sterically hindered organophosphite ligand comprises an oxide of an organopolyphosphite represented by the formula:

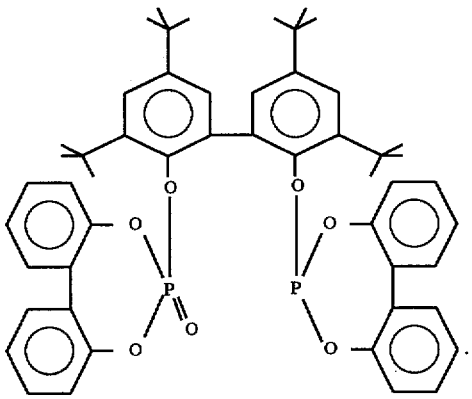

* * * * *